United States Patent [19]

Kessler

[11] 4,350,593

[45] Sep. 21, 1982

[54] ASSEMBLY, COMPOSITIONS AND METHOD FOR SEPARATING BLOOD

[75] Inventor: Stephen B. Kessler, North Bergen, N.J.

[73] Assignee: Becton, Dickinson and Company, Rutherford, N.J.

[21] Appl. No.: 51,976

[22] Filed: Jun. 25, 1979

Related U.S. Application Data

[63] Continuation of Ser. No. 861,676, Dec. 19, 1977, abandoned, which is a continuation-in-part of Ser. No. 802,724, Jun. 2, 1977, abandoned, which is a continuation of Ser. No. 665,964, Mar. 11, 1976, abandoned, which is a continuation-in-part of Ser. No. 629,707, Nov. 7, 1975, abandoned.

[51] Int. Cl.³ .................. B01D 21/26; C07F 7/18
[52] U.S. Cl. .................... 210/516; 210/782; 210/927; 23/230 B; 233/1 A
[58] Field of Search .............. 210/83, 84, 514–518, 210/DIG. 23, DIG. 24, 782, 927, 94; 23/230 B, 258.5, 259, 292; 128/2 F, 272.1, DIG. 5; 233/1 A, 1 R, 26; 422/72

[56] References Cited

U.S. PATENT DOCUMENTS

| | | | |
|---|---|---|---|
| 3,780,935 | 12/1973 | Lukacs et al. | 210/83 |
| 3,852,194 | 12/1974 | Zine | 210/83 |
| 3,920,549 | 11/1975 | Gigiello et al. | 210/83 |
| 3,920,557 | 11/1975 | Ayres | 210/83 |
| 3,997,442 | 12/1976 | Gigiello et al. | 210/DIG. 23 |
| 4,018,564 | 4/1977 | Wright | 210/DIG. 23 |
| 4,148,764 | 4/1979 | Lamont et al. | 210/516 X |

*Primary Examiner*—Thomas G. Wyse
*Attorney, Agent, or Firm*—Kane, Dalsimer, Kane, Sullivan and Kurucz

[57] ABSTRACT

The disclosure is of an improved assembly, compositions and method for the separation of blood into its light, liquid and heavy, substantially cellular phases with insertion of a non-Newtonian fluid between the phases as a barrier. The improvement comprises using as the non-Newtonian fluid, one which has substantially time independent rheological properties and a controlled yield stress value. The improved assemblies of the invention have enhanced shelf-lives and improved reliability of operation. The preferred assemblies may be sterilized by irradiation and the disclosure is also of a method for their manufacture.

10 Claims, 7 Drawing Figures

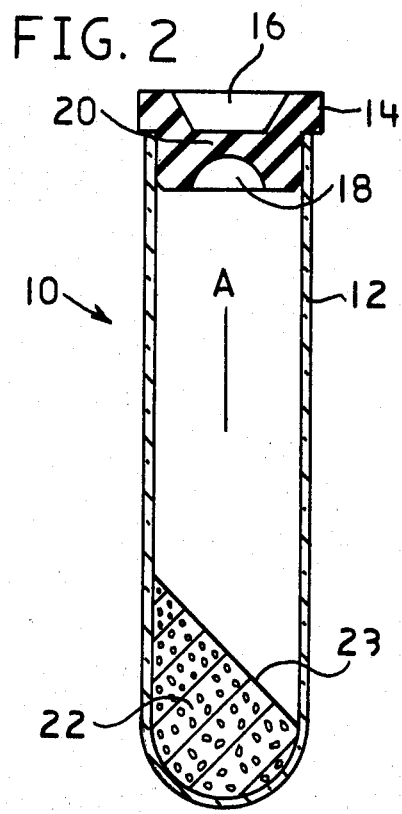
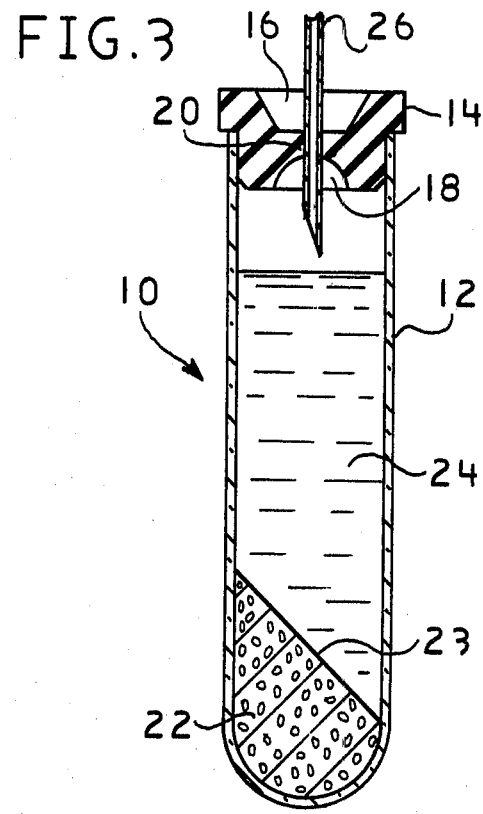
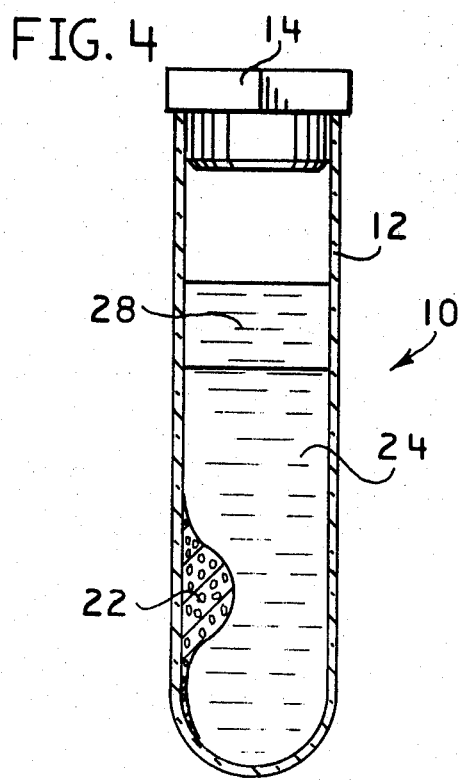
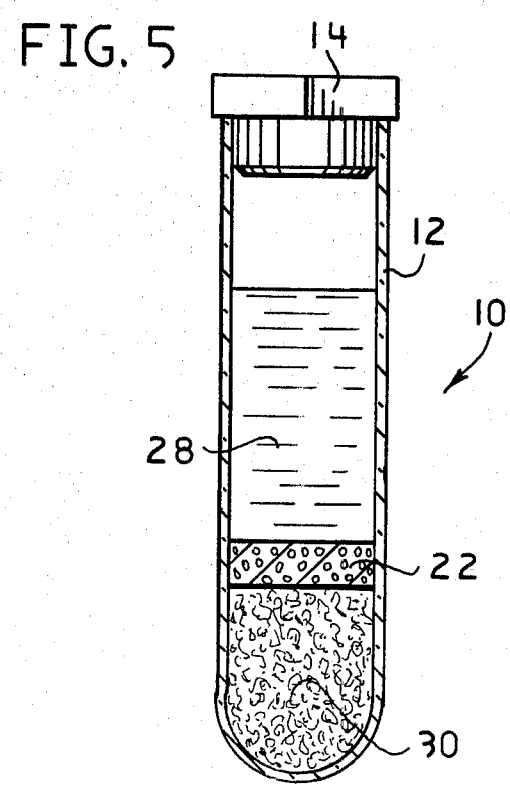

ASSEMBLY, COMPOSITIONS AND METHOD FOR SEPARATING BLOOD

CROSS-REFERENCE TO RELATED APPLICATIONS

This is a continuation of application Ser. No. 861,676, filed Dec. 19, 1977 now abandoned which was a continuation-in-part of copending U.S. application Ser. No. 802,724 filed June 2, 1977, now abandoned, and which was a continuation of U.S. application Ser. No. 665,964, filed Mar. 11, 1976, and now abandoned, and, which in turn was a continuation-in-part of then copending U.S. application Ser. No. 629,707 filed Nov. 7, 1975 and now abandoned.

BACKGROUND OF THE INVENTION

1. Field of the Invention

The invention is related to apparatus, compositions and methods for separating the phases of aqueous suspensions by centrifugal force and more particularly is related to the centrifugal separation of serum or plasma from whole blood.

2. Brief Description of the Prior Art

Prior hereto, blood separator devices have been known which employ non-Newtonian fluids as the separator barrier component; see for example U.S. Pat. Nos. 3,780,935 and 3,852,194 which employ barrier materials described as "gel-like" or "thixotropic".

In general, the blood separator devices of the prior art type employing a fluid separator component have not been entirely satisfactory in all respects. This is particularly true of pre-assembled units wherein the fluid barrier is initially disposed in the blood collection container component. Such pre-assembled units are subjected to handling, transportation and storage under a wide variety of environmental conditions prior to their use. Under handling, the fluid barrier component of some such assemblies may flow, coating the interior of the collection container, prior to operation of the device. This is undesirable because contact with the collection container (usually glass) facilitates the desired clotting of collected blood.

In the ideal blood separator of the type employing a non-Newtonian fluid as the phase separation barrier component, the fluid may be characterized as (1) compositionally stable, (2) physically stable in the absence of a substantial centrifugal force, (3) forming a strong, cohesive barrier, (4) chemically inert and (5) having a density intermediate between that of the separate blood phases. By compositionally stable, it is meant that the components or ingredients of the barrier material will not separate under normal storage and/or use. For example if the fluid separator is basically an oil or an oil-like composition compounded with an inert filler, the separator composition should be stable in that the oil or oil-like material should not bleed or separate from the inert filler dispersed therein. By physically stable, it is meant that the barrier material should not move or change shape except when subjected to a substantial centrifugal force. The barrier material, except when subjected to a substantial centrifugal force, should form a strong, cohesive body. By chemically inert, it is meant that the barrier material should not be chemically reactive with blood, its constituents or reagents commonly employed in carrying out diagnostic testing of blood serum.

My invention constitutes an improvement over the prior art in that I have provided a blood separator and blood separating compositions having the desired features of an ideal blood separator. The method of my invention provides a more reliable operative procedure. In addition and unexpectedly the compositions and assemblies of my invention are advantageously sterilized by exposure to ionizing radiation without significant degradation of composition or assembly.

SUMMARY OF THE INVENTION

The invention comprises, in a pre-assembled assembly for the collection and separation of blood into its light, liquid and heavy, substantially cellular phases under centrifugal force with establishment of a non-Newtonian fluid barrier between the separated phases, wherein said assembly comprises, a tubular container having an open end and a closed end, a removable closure for said open end, and a non-Newtonian fluid disposed in said container, the improvement which comprises; as said non-Newtonian fluid, a non-Newtonian fluid which has substantially time independent rheological properties and is composed of a non-silicone liquid whose viscosity is from 100 poise to 5000 poise (at 25° C.) compounded with 3 to 7 parts by weight of an inert filler blended therein.

The invention also comprises a method of separating blood into its component light and heavy phases employing the assembly of the invention, compositions useful in such separations and the method of preparing sterile assemblies.

The term "non-Newtonian fluid" is used throughout the specification and claims in its normally accepted sense as meaning a fluid for which the flow curve (shear stress versus shear rate) is not linear through the origin at a given temperature and pressure: see A. Skelland, Non-Newtonian Flow and Heat Transfer, John Wiley & Sons, Inc., New York, N.Y., page 4–5.

The term "non-Newtonian fluid which has substantially time independent rheological properties and a yield stress value" as used herein means a material characterized rheologically by a yield stress below which flow is 0 or negligibly small and at higher stresses behaves like a liquid whose viscosity may or may not be shear rate dependent but is substantially time independent.

The improved separator assembly of the invention has an improved shelf-like and reliability in operation over the prior art assemblies.

BRIEF DESCRIPTION OF THE DRAWINGS

FIG. 2 is a cross-sectional side elevation of an embodiment of the improved assembly of the invention.

FIG. 3 is a view as in FIG. 1 following filling of the assembly with blood.

FIG. 4 is a view as in FIG. 2 but during centrifugation of the filled assembly.

FIG. 5 is a view as in FIG. 3, but following completion of separation of centrifugation.

DETAILED DESCRIPTION OF THE PREFERRED EMBODIMENTS OF THE INVENTION

Figure 1:
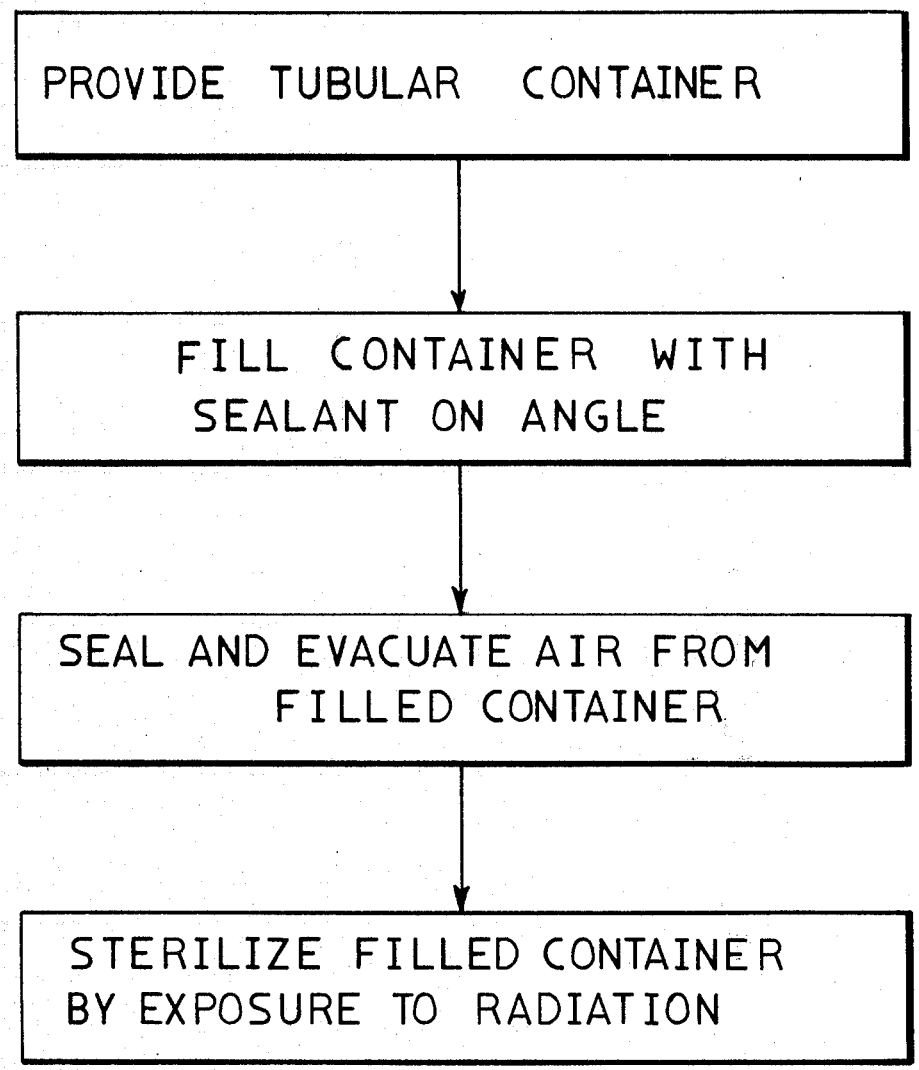
FIG. 1 is a diagram of a flow process for making assemblies of the invention.

FIG. 1 is a flow chart showing schematically a preferred embodiment process for the manufacture of assemblies of the invention. Thus, the initial step is to provide a tubular container of the type suitable and conventionally used to collect and store blood specimans. In the next step of the preferred process, a sealant barrier material, which will be described in greater detail hereinafter, is positioned within the tubular container. Most preferably the sealant barrier is disposed at the closed end of the tubular container, with the upper surface of the barrier disposed at an angle i.e., the unconfined surface of the barrier material is formed in a plane which is not perpendicular to the long axis of the tubular container. This will be described in greater detail hereinafter.

The sealant barrier material may be disposed in the tubular container employing conventional apparatus and technique. Examples of the apparatus which may be used for dispensing the barrier material are reciprocating pumps or auger-type pumps which are used for handling paste-like materials. The pump in turn feeds material to a valve which meters the proper quantity of material into each tubular container. Following disposition of the sealant barrier material in the tubular container, the container may be air-evacuated and sealed in the manner known to the art. Alternatively, insertion of the sealant barrier material, air-evacuation and sealing may be carried out simultaneously or near simultaneously with the use of conventional and known fluid-filling apparatus.

Once the tubular container has received the barrier component and has been air-evacuated and sealed, it is desirably sterilized, that is freed of bacterial contamination within the tube. In the preferred process of the invention this is accomplished by irradiation of the assembly of the invention with ionizing radiation. Representative of ionizing radiation is radiation with X-ray, electron beam, gamma ray and like radiation. The sterilizing technique is well known as is the apparatus for sterilization. Unexpectedly the preferred compositions of the invention are not significantly affected by irradiation. This is a particular advantage over many of the prior art barrier materials which may be substantially degraded by irradiation, i.e.; their decomposition is accelerated.

A complete understanding of the invention is conveniently obtained by referring to the accompanying drawings of FIGS. 1-7, inclusive.

FIG. 2 is a cross-sectional side elevation of an embodiment assembly of the invention and shows apparatus 10 which comprises a tubular container 12 having one open end and one closed end. The open end of tube 12 is sealed with gas-proof closure 14 which has an upper axial recess 16 and a lower axial recess 18 separated by a thin, cannula penetrable zone 20. Disposed adjacent the lower closed end of tube 12 is barrier material 22. The unconfined (by the container walls) surface 23 of barrier 22 forms a surface which is not a plane which is perpendicular to the long axis A of the tube 12. Preferably, surface 23 forms an angle of from about 5° to about 60° with the plane normal to the longitudinal axis A of tube 12. Most preferably, the angle formed is from about 10° to about 20°. In the assembly 10 of the invention, barrier 22 must possess rheological properties such that it will remain stationary during shipping and storage yet flow like a liquid under substantial centrifugal forces. I have found that a barrier 22 which meets this requirement is a non-Newtonian fluid which has substantially time independent rheological properties.

Preferred barrier materials 22 will have a yield stress value of from about 200 to about 4000, preferably 400 to 2500 and most preferably from about 600 to about 1000 dynes/cm$^2$. A barrier 22 having a lower yield stress value may not remain stationary under all conditions to which the assembly 10 may be subjected prior to use, i.e.; during handling and storage. On the other hand, if the yield stress value is above about 4000, the barrier 22 may not flow like a liquid under normal centrifugation, i.e.; centrifugal forces employed in the conventional separation of blood (on the order of from about 700 to 1200 gravities).

In the preferred embodiment assembly of the invention, a barrier 22 having a relatively high yield stress value, i.e.; on the upper side of the above-specified range, may not flow immediately under normal centrifugal forces if the upper surface 23 is a plane perpendicular to the axis A of the tube 12. This is because the shear stress developed under the preferred normal centrifugal forces is less than the yield stress of the barrier material and is due to the symmetry of the configuration of the disposed barrier 22. Under such circumstances, increasing the cenrifugal force is not desirable or practical since it may result in the rupture of cellular blood components with the consequent release of cellular fluids or may not be possible due to limitations of available centrifuging equipment. To overcome this situation, the preferred assembly of the invention comprises one as illustrated in the assembly 10 wherein barrier material 22 is disposed as shown in FIG. 2 with the surface 23 forming other than a plane perpendicular to the axis A of the tube 12.

As stated above, barrier 22 may be any non-Newtonian fluid which has substantially time independent rheological properties and preferably a yield stress value within the range of from about 200 to about 4000 dynes/cm$^2$. As also stated above, the barrier 22 should be a composition which is inert, i.e.; does not react with blood, the separated phases of blood or reagents commonly employed in diagnostic procedures carried out on the separate blood phases. In addition, the barrier material 22 must have a specific gravity intermediate between those of the light liquid and the heavy, substantially cellular phases of blood. In general, the specific gravity should be within the range of from about 1.03 to about 1.09. Preferably, the specific gravity should be within the range of from about 1.04 to about 1.06.

Those skilled in the art will realize that a wide variety of materials may be employed as the barrier 22. In general, the preferred barriers 22 are blends of a non-silicone liquid component with an inert filler to obtain a non-Newtonian fluid of the desired density, viscosity and yield stress value.

The liquid component must have a viscosity in the range of 100 poise to 5000 poise. The preferred range is 1000 poise to 3000 poise. Examples of non-silcone liquids which may be used in preparing barrier 22 materials (of the invention) are mineral oils, synthetic hydrocarbon oils, high molecular weight esters of dicarboxylic acids or perfluoro polymeric fluids such as trifluorochoroethylene polymers and the like. Solutions of high (molecular weight) polymers in oils or other solvents of low volatility may also be used. The latter should fall within the viscosity range previously stated and preferably have a density between 1.007 and 1.067 grams per cubic centimeter. The most preferred density range is 1.017 to 1.037 grams per cubic centimeter, assuming the preferred fillers hereinafter described are used.

Particularly preferred liquid components of the non-Newtonian fluids employed in the apparatus and the method of the invention are liquid, polymeric, polyesters of polycarboxylic acids and polyhydric alcohols, having the above described viscosity. In addition, the polyesters should be inert in respect to blood and blood components, i.e.; substantially non-reactive therewith. The preparation of such polyesters is well known to those skilled in the art. In general, they may be prepared by the condensation of substantially equivalent proportions of polycarboxylic acids and polyhydric alcohols, e.g.; polyols. Representative of dicarboxylic acids which may be employed are succinic acid, adipic acid, suberic acid, azelaic acid, sebacic acid, phthalic acid, isophthalic acid, terephthalic acid and like unsaturated dicarboxylic acids their esters or anhydrides thereof where the anhydrides exist.

Illustrative of the diols which may be employed to prepare the above-described polyesters are ethylene glycol, diethylene glycol, polyethylene glycol, dipropylene glycol, or polypropylene glycol, 1,2-butanediol, 2,3-butanediol, 1,4-butanediol, 1,3-butanediol, neopentyl glycol, mixtures thereof and the like.

The condensation of diacid and diol may be carried out by esterification or transesterification using conventional apparatus. In general it may be effected by admixing the two reactants and heating the admixture. Heating may be carried out in the presence of a catalytic proportion of a condensation catalyst. Representative of condensation catalysts which may be used are zinc acetate, calcium acetate, yellow lead oxide, dibutyl tin oxide and the like. The catalyst is employed in a catalytic porportion, which is generally within the range of from about 0.0001 to about 1.0 percent by weight of the starting reactants. The heating step may be carried out over a wide range of temperatures, i.e.; from about 70° C. to about 300° C. with or without the application of vacuum. Preferably the heating step is carried out under an inert gaseous atmosphere such as a nitrogen gas. During the reaction it is advantageous to remove one product of condensation, as it forms. Thus, removal of water, alcohol or diol may be carried out by conventional techniques well known to those skilled in the art, for example by sparge or distillation.

The time required to complete the condensation of dicarboxylic acid and diol varies depending on the nature of the reactants, catalyst and reaction temperature used. Progress of the reaction is observable by periodic analysis to determine the acid number of the reaction mixture, measuring the viscosity of the melt, or volume of the eliminated product.

Upon completion of the reaction, the desired polyester may be purified by transesterification.

The inert filler component used to compound the barrier 22 materials of the invention may be any of those well known fillers previously employed in the art to prepare a grease. The preferred filler is a finely divided fumed silica which has been treated to render it hydrophobic. Examples of such treated filler materials are well known; see for example U.S. Pat. Nos. 2,938,009; 3,037,933; 3,526,594; 3,635,743; and 3,847,848. The silicas used should have specific surface areas in the range of 100 to 400 square meters per gram.

In the more preferred embodiment of the present invention the silica filler is one treated with a silane. preferred silane treating agents for the silica fillers whether precipitated or fumed silica are dimethyl dichlorosilane or trimethylchlorosilane. An example of such a treated silica is the commercially available Aerosil R-972 (Degussa, Inc.).

It is desired that per 100 parts of the viscous fluid component polymer, specie blends or polymer species, within the preferred density range as specified above, that there be utilized from 3 to 7 parts of total filler component. Generally if less than 3 parts of filler is utilized in the composition the composition will not have a sufficient consistency to function as desired in the apparatus of the invention. If more than 7 parts by weight of, for example, a silica filler is utilized in the barrier 22 composition then the composition may suffer from several disadvantages. More specifically, the increased specific gravity and increased yield stress in compositions having higher proportions of silica filler require higher centrifugation speeds to operate, resulting in the rupture of red blood cells. Further, most hospitals or physicians' offices lack the higher speed equipment which would be needed.

Further improvement in the composition of the barrier 22 material may be realized through the addition of a stabilizer of the formula, $$R'O\text{---}(C_aH_{2a}O)_{\overline{x}}(C_bH_{2b}O)_{\overline{y}}H$$

where $R'$ is a monovalent hydrocarbon radical and is preferably selected from the class of hydrogen and lower alkyl radicals having from 1 to 7 carbon atoms, such as methyl, ethyl, propyl, butyl, pentyl, hexyl and heptyl including isomeric forms thereof, a and b are integers equal to from 1 to 4, inclusive, x is an integer equal to from about 4 to 50 or more and y is a whole number equal to from 0 to 50. Such polyethers are well known compounds and are sold by various tradenames and various molecular configurations by many chemical companies such as, for instance, as is used in Example 2 of U.S. Pat. No. 3,037,933 (a liquid monobutylether of a mixed polyethylene-polypropylene glycol; UCON LB 1145, Union Carbide Corp.). Preferably, there is utilized in the above compositions from 0.01 to 2 parts by weight of the above polyether stabilizing compounds, per 100 parts of the liquid component.

In selecting barrier 22 materials, the yield stress value may be determined by rheological measurement. The rheological properties for the barrier 22 materials may be measured using a Weissenberg rheogoniometer with cone plate geometry. Flow curves are obtained with this apparatus by varying the shear rate linearly starting from 0, increasing with time and then decreasing back to 0. The shear rate range used for these measurements is from 0 to 2 sec$^{-1}$. The flow curve thus obtained is a graph of shear stress versus shear rate. To obtain yield stress values the data from these curves must be treated with a curve fitting equation. The one used in this instance is authored by Ching-Rong Huang and presented in "A Thermodynamic Approach to Generalized Rheological Equations of State for Time Dependent and Time Independent Non-Newtonian Fluids", Chemical Engineering Journal, vol. 3, (1972). The equation is presented below in its time independent form as:

$$\tau - \tau_0 = \mu\dot{\gamma} + AC\dot{\gamma}^\eta e^{-C\dot{\gamma}\eta} \quad (I)$$

wherein $\tau$ is the shear stress, $\tau_o$ is the yield stress, $\mu$ is the Newtonian part of the viscosity, A the equilibrium constant of the distribution of aggregated and non-aggregated gel, C the rate constant of the physical degradation of the aggregated gel, $\eta$ the order of the degradation reaction and $\dot{\gamma}$ is the shear rate. The data is analyzed using a curve fitting program.

Figure 6:
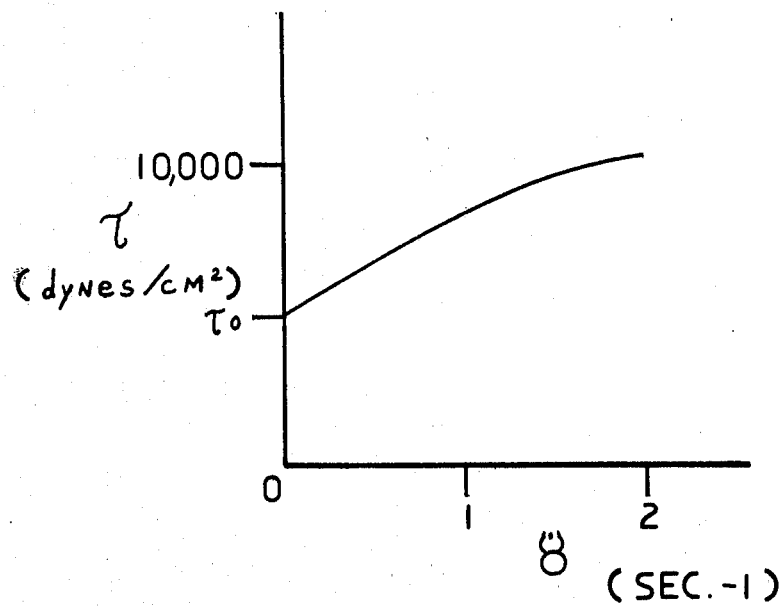
FIG. 6 is a flow curve for a pseudoplastic with yield value.
Figure 7:
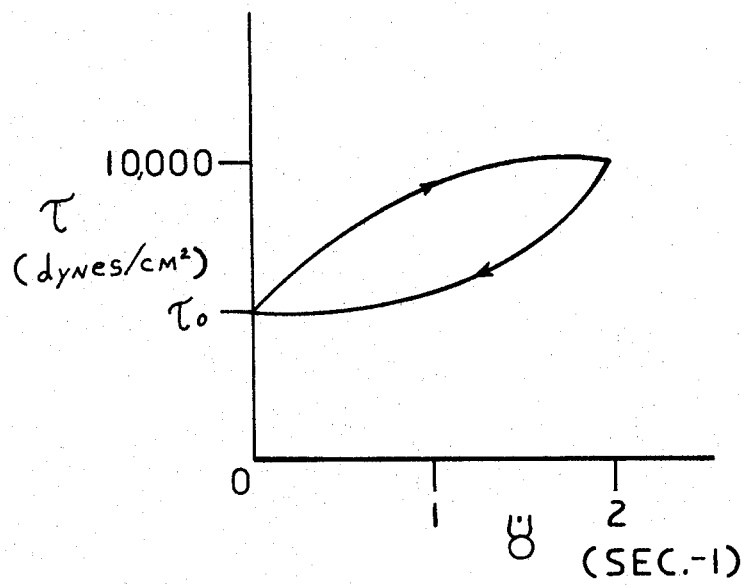
FIG. 7 is a flow curve for a thixotrope which demonstrates time dependency.

Specific models of time independent non-Newtonian fluids which will meet the requirement of barrier 22 as stated above are: the Bingham plastic, the pseudo-plastic with yield value (see FIG. 6, illustrating the flow curve developed by a pseudo-plastic with yield value. The curve is in contradistinction to that of a thixotrope, which demonstrates time dependency; see FIG. 7.) and the dilatant fluid with yield value. Fluids which display the characteristics of these models and have yield values in the correct range will function in the preferred assembly of the invention as a barrier 22 component.

A particularly preferred blood separating assembly of the invention is one wherein the barrier 22 is a material resistant to aging, sedimentation and bleeding. Aging refers to the tendency of some non-Newtonian fluids to harden over a period of time, thereby developing an unsatisfactory and high yield stress value. Sedimentation is the tendency, in a two component material, for the inert filler particles to precipitate out of the fluid. Such precipitation alters the density of the fluid and is of course undesirable for density gradient separations. Bleeding is the propensity of the liquid component of the two component barrier 22 compositions to separate. Aging, bleeding and sedimentation occur over periods of time and affect the shelf-life of the assembly 10 if they occur too rapidly. If they occur too rapidly, the rheological properties of the barrier 22 are adversely affected.

As an indication of how a given barrier 22 material will perform after the assembly 10 is stored under normal conditions for a period of time, for example after from 1 to 2 years, the material may be tested for bleed and sedimentation characteristics. The test comprises accelerating the bleed and sedimentation processes by ultra-centrifuging an aliquot of the barrier 22 material. The sample undergoes an acceleration of 250,000 X gravity for a period of four hours. Any liquid which has separated is removed and the weight of the separated liquid is expressed as a percentage of the weight of the starting material. In the preferred barrier 22 component materials, the percent of bleed is less than 5 percent, preferably less than 3 percent for the longest shelf-life for assembly 10.

The sample from the ultracentrifuge may also be checked for sedimentation. Where sedimentation is severe, there is a visible layer of opaque material present in the tube. A quantitative measure of the degree of sedimentation can be obtained by comparing the specific gravities of the material at the top and bottom of the ultracentrifuge tube. This is done by removing a small quantity of the material from top to bottom, respectively, of the ultracentrifuge tube and dropping it into a density gradient column (ASTM test D-1505). In the preferred assembly 10 of the invention, sedimentation of the composition forming barrier 22 is minimal and the specific gravity difference between material at the top and at the bottom of the ultracentrifuge tube, according to the above procedure, is less than about 0.03, preferably less than about 0.005.

A barrier 22 composition particularly preferred as a component of the assembly 10 is one prepared as follows:

EXAMPLE 1

(A) An appropriate reaction vessel is charged with 7 moles of azelaic acid, 5.25 moles of neopentyl glycol and 2.1 moles of 1,3 butanediol. The charge is heated with stirring under flowing nitrogen sparge to remove the water produced by the esterification. After approximately 14 moles of water are collected, vacuum is applied, heat is increased to produce transesterification, with the excess of glycols being collected. The reaction is completed when the acid number of 0.4 is reached, a hydroxyl number of 14.4, a viscosity of 600 poise at 25° C. and a density of 1.05 at 25° C.

(B) To 100 parts of the above prepared polyester of step (A) there is added with stirring 3 parts of treated fumed silica (Degussa R-972) and 1 part of UCON LB 1145 (Union Carbide, supra.). When the resulting barrier material is tested for its bleed and yield stress value by the methods described above, they are found to be satisfactory.

EXAMPLE 2

Similarly, repeating the procedure of Example 1, part (B) but employing the polyester obtained by reaction of azelaic acid with a 5:2 (molar) mixture of neopentyl glycol and butanediol, said polyester having an acid number of 0.4, a viscosity of 2000 poise and a density of 1.025, and increasing the proportion of fumed silica to 4 parts, there is obtained a barrier material with less than 1% bleed (after ultracentrifuging at 250,000 X g for 4 hours) and a yield stress value of circa 500–600 dynes/cm².

The barrier preparation retains the desired rheological properties for at least 1 year when stored at temperatures between 4° C. to 40° C. and may be sterilized by ionizing radiation, without significant effect.

The above example describes the manner of making the invention and is the best mode contemplated by the inventor but is not to be construed as limiting.

The method of the invention is carried out according to the following procedure. An assembly of the invention such as assembly 10 is provided and may be initially air evacuated to form a vacuum therein. The apparatus 10 of FIG. 2 is then conveniently filled as shown in FIG. 3 by introducing a proportion of blood 24 via a blood-bearing cannula 26 inserted through the thin cannula penetrable zone 20 of closure 14. The blood filled apparatus 10 is then centrifuged in a conventional manner so as to apply sufficient force to cause a separation of the blood 24 into its light liquid phase 28 and its substantially cellular portion 30. During the course of separation and due to the surface 23 configuration of barrier 22 material, barrier 22 migrates from its initial position adjacent the closed end of container 12 to seek its density gradient level under the centrifugal force applied. The initial migration of barrier 22 is shown in FIG. 4, a cross-sectional side elevation as seen in FIG. 3 but following partial separation of the blood into its component parts 28 and 30 under centrifugal force. Thus blood 24 has been partially separated into a light phase 28 of serum or plasma and barrier 22 has, at this point begun to migrate to its density gradient level.

FIG. 5, a cross-sectional side elevation as shown in FIG. 4 but after completion of centrifugation shows the complete separation and isolation of the light, liquid phase 28 from the heavy, substantially cellular phase 30. As shown in FIG. 5, barrier 22 has inserted itself at the interface between the separated blood phases 28 and 30. At this point, the applied centrifugal force may be terminated and the assembly 10 may be removed from the centrifuge. Barrier 22 forms a rigid, cohesive barrier between the separated blood phases. In this position, the closure 14 may be removed to decant or otherwise remove the separated light phase 28 when desired. Alternatively, the separated blood may be stored with barrier 22 remaining fixed-in and-between the phases without fear that the separated phases will become admixed by handling.

The advantage of the method of the invention resides in its reliability as a consequence of employing the highly reliable, long shelf-life assembly of the invention.

The light liquid portion of blood is referred to as blood serum if the blood has clotted or plasma if the blood has not clotted. The heavy, substantially cellular portion of the blood is the residue remaining after separation of the blood serum or plasma.

What is claimed:

1. In a pre-assembled assembly for the collection and separation of blood into its light, liquid and heavy, substantially cellular phases under centrifugal force with the establishment of a non-Newtonian fluid barrier between the separated phases, wherein said assembly comprises, a tubular container having an open end and a closed end, a removable closure for said open end, and a non-Newtonian fluid disposed in said container, the improvement which comprises; as said non-Newtonian fluid a blend of from about 93 to 97 parts of a polyester prepared by the condensation of equal molar proportions of azelaic acid with a mixture of neopentyl glycol and butanediol in a molar ratio of 5:2 and having a viscosity of from 100 to 5,000 poises and a density of from 1.007 to 1.067 gms/cc with from 3 to 7 parts by weight of a fumed silica, said blend having a specific gravity of from 1.03 to 1.09 and said fluid having substantially time independent rheological properties, said non-Newtonian fluid being inert in respect to chemical reactivity toward blood and blood components.

2. The assembly of claim 1 wherein said fluid has a yield stress value within the range of from about 200 to about 4000 dynes/cm².

3. The assembly of claim 1 having a further improvement wherein said non-Newtonian fluid which has substantially time independent rheological properties is initially disposed adjacent said closed end so that said non-Newtonian fluid having substantially time independent rheological properties has a single unconfined surface and said surface is not a plane which is perpendicular to the longitudinal axis of said tubular container.

4. The assembly of claim 3 wherein said unconfined surface is on a plane which forms an angle of from about 5° to about 60° with the plane normal to said axis.

5. The assembly of claim 4 wherein said angle is from about 10° to about 20°.

6. The assembly of claim 1 wherein said blend has a bleed of less than 1.0 percent when ultracentrifuged at 250,000 X g for 4 hours.

7. The assembly of claim 1 wherein said fluid includes from 0.05 to 3 parts by weight of a stabilizing compound of the formula,

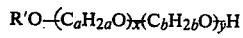

where R' is a member selected from the class consisting of hydrogen and lower alkyl radicals having from 1 to 7 carbon atoms, a and b are integers equal to from 1 to 4, inclusive, x is an integer equal to from about 4 to 50 or more and y is a whole number equal to from 0 to 50.

8. The assembly of claim 7 wherein the stabilizing compound is present at a concentration of 0.1 to 2 parts by weight.

9. A composition, which comprises;
from 93 to 97 parts by weight of a fluid polymeric polyester prepared by the condensation of substantially equimolar proportions of azelaic acid and a mixture of neopentyl glycol and butanediol in a molar ratio of 5:2, said polyester having a viscosity of from 100 to 5000 poises at 25° C. and a density of from 1.007 to 1.067; and
from 3 to 7 parts by weight of a fumed silica.

10. A method of providing an assembly for the separation of blood into its light, liquid and heavy, substantially cellular phases under centrifugal force with establishment of a non-Newtonian fluid barrier between its separated phases, which comprises;
providing a tubular container having an open end and a closed end;
depositing adjacent the closed end a barrier material which comprises an inert non-Newtonian fluid which has substantially time independent rheological properties, a density of from about 1.03 to 1.09 and comprises from 93 to 97 parts of a polymeric polyester liquid having a viscosity of from 100 to 5000 poises at 25° C. and a density of 1.007 to 1.067, said polyester being the condensation product of substantially equal molar proportions of azelaic acid with a mixture of neopentyl glycol and 1,3-butanediol in a molar ratio of 5:2 compounded with from 3 to 7 parts by weight of a fumed silica filler.

* * * * *